United States Patent [19]
Abys et al.

[11] Patent Number: 5,228,976
[45] Date of Patent: Jul. 20, 1993

[54] HYDRODYNAMICALLY MODULATED HULL CELL

[75] Inventors: Joseph A. Abys, Warren; Igor V. Kadija, Ridgewood, both of N.J.

[73] Assignee: AT&T Bell Laboratories, Murray Hill, N.J.

[21] Appl. No.: 550,266

[22] Filed: Jul. 9, 1990

[51] Int. Cl.$^5$ .......................................... G01N 27/42
[52] U.S. Cl. ............................. 204/434; 204/DIG. 7; 204/212; 204/400
[58] Field of Search ................ 204/290 F, 400, 434, 204/DIG. 7, 212

[56] References Cited

U.S. PATENT DOCUMENTS

| | | | |
|---|---|---|---|
| 2,149,344 | 3/1939 | Hull | 204/153.1 |
| 2,760,928 | 8/1956 | Ceresa | 204/434 |
| 2,801,963 | 8/1957 | Hull et al. | 204/434 |
| 2,859,166 | 11/1958 | Grigger | 204/DIG. 7 |
| 3,121,053 | 2/1964 | Hull, Jr. et al. | 204/434 |
| 3,215,609 | 11/1965 | Chapdelaine | 204/434 |
| 3,278,410 | 10/1966 | Nelson | 204/290 F |
| 3,281,338 | 10/1966 | Leary et al. | 204/290 F |
| 3,356,597 | 12/1967 | Schmidt | 204/434 |
| 3,616,287 | 10/1971 | Draghicescu et al. | 204/DIG. 7 |
| 4,102,770 | 7/1978 | Moriarty et al. | 204/212 |
| 4,252,027 | 2/1981 | Ogden et al. | 73/826 |
| 4,605,626 | 8/1986 | Beck | 204/403 |

OTHER PUBLICATIONS

Patent Abstracts of Japan, vol. 10 No. 271 (P-497) [2327] Sep. 16, 1986; & JP-A-61 95 242 (Toyota Motor Corp.) May 14, 1986.

A. J. Arvia, et al, "Mass Transfer in the Electrolysis . . . ", Electrochimica Acta, 1962, vol. 7, pp. 65-78, Pergamon Press, Ltd.

Walter Nohse, et al., "The Investigation of Electroplating and Related Solutions with the Aid of the Hull Cell", Robert Draper, Ltd., Teddington, England (1966), pp. 17-25.

W. Michael Lynes and Uziel Landau, "A Novel Adaptation of the Finite Difference Method for Accurate Description of Non-Orthogonal Boundaries", The Electrochemical Society, Fall Meeting, Chicago, 1988, Abstract 332.

R. O. Hull, "Current Density Range Characteristics—Their Determination and Application", Proc. Amer. Electroplaters Society, 27 (1939), pp. 52-60.

J. S. Newman, Electrochemical Systems, Prentice-Hall, Inc., Englewood Cliffs, N.J. (1973), pp. 2-9, 307-309.

*Primary Examiner*—T. Tung
*Attorney, Agent, or Firm*—Oleg E. Alber

[57] ABSTRACT

The invention provides, in electroplating quality control methods for manufacturing, better similarity and relevance between a Hull Cell quality control test and a particular plating operation. The invention is a simple and yet functional instrument which can be used to identify the performance of the plating bath prior to manufacturing operation under similar hydrodynamic conditions. The instrument is a rotating cylinder with a flexible Cu test panel attached to its surface. Like a Hull Cell, a range of current density can be simultaneously applied. Unlike a Hull Cell, the rotating speed of the cylinder and hence the solution agitation is practically unlimited. The operator can identify the operating window for the particular process and apply them to the production line. The instrument has also demonstrated usefulness in developing proprietary electroplating chemistries.

10 Claims, 14 Drawing Sheets

STANDARD HULL CELL

10 CM/S
HMH CELL

100 CM/S
HMH CELL

STANDARD HULL CELL

10 CM/S
HMH CELL

100 CM/S
HMH CELL

HYDRODYNAMICALLY MODULATED HULL CELL

FIELD OF THE INVENTION

This invention concerns with an apparatus for control of electrodeposition performance of a plating bath prior to and during manufacturing operation.

DESCRIPTION OF THE PRIOR ART

Electroplating encompasses many scientific disciplines including electrochemistry, hydrodynamics and transport phenomena, organic and inorganic chemistry, materials science, and metallurgy, which, in turn, involves an appropriate selection of testing equipment and operating parameters. One of the most critical parameters of electroplating is the interfacial transport and its relation to current density. Once the choice for the bath composition has been narrowed down, the definition and the selection of current densities and transport conditions become critical factors which determine the bath performance and the plated product properties. To this end, several advanced techniques are being used in electrochemical research and development.

Rotating electrodes, such as rotating discs, disc-rings, ring-ring electrodes and rotating cylinders, create a defined hydrodynamic condition in the operating cell while the electrochemical measurements are being performed giving, in each experiment, information on a single current density. However, with few rare exceptions, the range of current densities in plating processes is typically wide. Ten to twenty percent variation from the nominal current density for more simple and up to 200 percent for more complex parts command a wide range of functional efficiency of the plating process. Under such conditions, information needed concerning the effect of a broad range of current densities requires numerous tests.

Hull cell, developed by R. O. Hull in 1939 as a quality control and developmental tool, permits in a single test to preview a range of current densities which provide a desired plating characteristic at a given total current. The Hull cell is described in R. O. Hull, "Proceedings of American Electroplaters Society", 27 (1939), pp 52-60 and in U.S. Pat. No. 2,149,344 issued to R. O. Hull on Mar. 7, 1939. Also see a book by Walter Nohse et al. entitled "The Investigation of Electroplating and Related Solutions with the Aid of the Hull Cell", Robert Draper Ltd., Teddington, England, 1966, especially pages 17-25.

The Hull cell is schematically represented in FIG. 31. The Hull cell, generally designated as 310, is a four-sided, flat bottomed container, 311, of certain capacity (typically in mls.) in which flat vertically positioned an anode, 312, and a cathode, 313, are arranged at an angle each to another. Typically, cathode is also at an angle to both of two side walls, 314 and 315, of the container. The test panel is only partially submersible in an electrolyte, 316. Several sizes of Hull cells are commerically available with solution capacities of 250, 267, 320, 534 and 1000 mls. The unique feature of the Hull cell, due to the arrangement of the anode to cathode geometry, is its ability to electrodeposit on the test panel a metal across a range of current densities depending on the total applied current. The current densities range from low current density at that end of cathode 313 which forms an acute angle with wall 314 to high current density at the end of the cathode forming an obtuse angle with wall 315. In FIG. 32 is represented a theoretical current density distribution in a typical standard Hull cell with applied total current of 2A.

The characteristic design feature of the Hull cell is the acute angle between anode 312 and cathode 313 combined with the effect of cell wall 314 making the acute angle to the cathode at the low current density end portion of cathode 313. The angle between the electrodes and the shielding of the cell wall 314 provide the current density distribution. At the low current end where wall 314 is at an acute angle to the cathode, the primary current density is infinitely small. Towards the center of the panel the current increases gradually reaching its maximum at the high current density end. A pattern of deposits obtained at this wide range of current densities is used as an indicator of the quality of the product that can be obtained if the plating is performed at any nominal current density within the given range. In a single test one can select a range of current densities which provide desired plating characteristics. However, the use of the Hull cell is limited, especially under high liquid velocity conditions, due to the lack of mass transfer control, uneven deposition rate at specified current densities and lack of high speed liquid mixing. In an experiment with varying hydrodynamics and mass transport along the panel, the obtained patterns could be a result of both current density and hydrodynamic conditions. Such a result would be irrelevant to the operating conditions and could not be used as a guide in bath performance evaluation.

A typical range of current densities and mixing conditions for a specific electroplating process is usually defined in the operating manual for that process. In order to keep the production quality at the specified level, operators perform a quality control tests at regular intervals employing the Hull cell. Based on such tests, corrective actions are applied to maintain the bath electrodeposition performance. Unfortunately, regardless of many common denominators, in most instances the pattern obtained is a result of vaguely defined variables such as the mixing speed, location of the stirring bar, preparation of the sample and others.

Irreproducible and limited solution agitation is usually provided in a Hull cell by a fixed rate reciprocating paddle, a magnetic stirrer or a forced gas mixing near the cathode/solution interface. By using such an arrangement, it is difficult to obtain consistently reproducible results and to correlate these to a manufacturing operation where the solution agitation can vary significantly depending upon the application and the desired plating rate. For example, in barrel plating operations the solution is barely moving relative to the work piece while in jet plating applications the solution velocity can reach several meters per second. Over such a wide range of hydrodynamic conditions, the effects of chemical equilibria, additives, contaminants and other components of the plating solution on the quality of the product can vary considerably.

Particularly important is the interpretation of the effects of impurities on the pattern appearance such as peeling, dullness, or black deposit at low current density end of the panel. These symptoms will vary depending on the mixing conditions of the cell. However, the Hull cell apparatus is limited in providing information regarding a specific plating process which may be affected by variations in solution agitation.

Furthermore, in many instances, particularly in modern plating facilities, high speed plating baths with liquid velocity of several meters per second are being employed. For such conditions, information developed on the basis of the interpretation of a Hull cell panel obtained at typical Hull cell liquid velocities of 20–30 cm/sec. could be meaningless. Use of the Hull cell with higher mixing rates leads to spillage and usually gives little clue on the solution performance.

Another uncertainty is connected with inconsistencies in current density distribution. Hull cell panels are usually interpreted with the scale of current densities that are attributed to the position on the panel. The position of the liquid meniscus on one side and the vicinity of the cell bottom on the other side of the panel may influence the rate of deposition. As a result, the thickness distribution at each current density designation can vary considerably leading to erroneous interpretation. Such variations result form an uneven current distribution which is inherent to the Hull cell design and can significantly affect the reproducibility and the accuracy of panel interpretation leading to losses in production and disorientation in R & D efforts.

Unfortunately, there are no viable alternatives to the Hull cell, today. Therefore, it is desirable to have a device which combines, in a single unit, controlled cell hydrodynamics and resulting uniformity of mass transport at the panel interface with the capability of measuring wide range of current densities on a single experiment. Only in such experimental conditions, patterns obtained on the panel would reflect the expected performance of the process at specified mixing rate.

SUMMARY OF THE INVENTION

This invention is a Hydrodynamically Modulated Hull cell (hereinafter referred to as "HMH cell") which can be used for quality control and for developmental applications and which combines, in a single unit, the capability of providing for well-defined cell hydrodynamics and measuring wide range of current densities on a single experiment.

The HMH cell utilizes an elongated, cylindrically shaped measuring instrument in which a cathode and an anode are vertically spaced along a central longitudinal axis of the instrument, forming a single coaxially arranged unit with the anode being below the cathode. The instrument is capable of being rotated about its longitudinal axis. This permits one to vary in a controlled manner the solution agitation while effectively applying a panel size and current density range typical for a standard Hull cell. This apparatus can be used to establish the functionality of electroplating solutions in the liquid velocity range of the electrolyte from quasi stationary to up to several meters per second.

DETAILED DESCRIPTION

Figure 1:
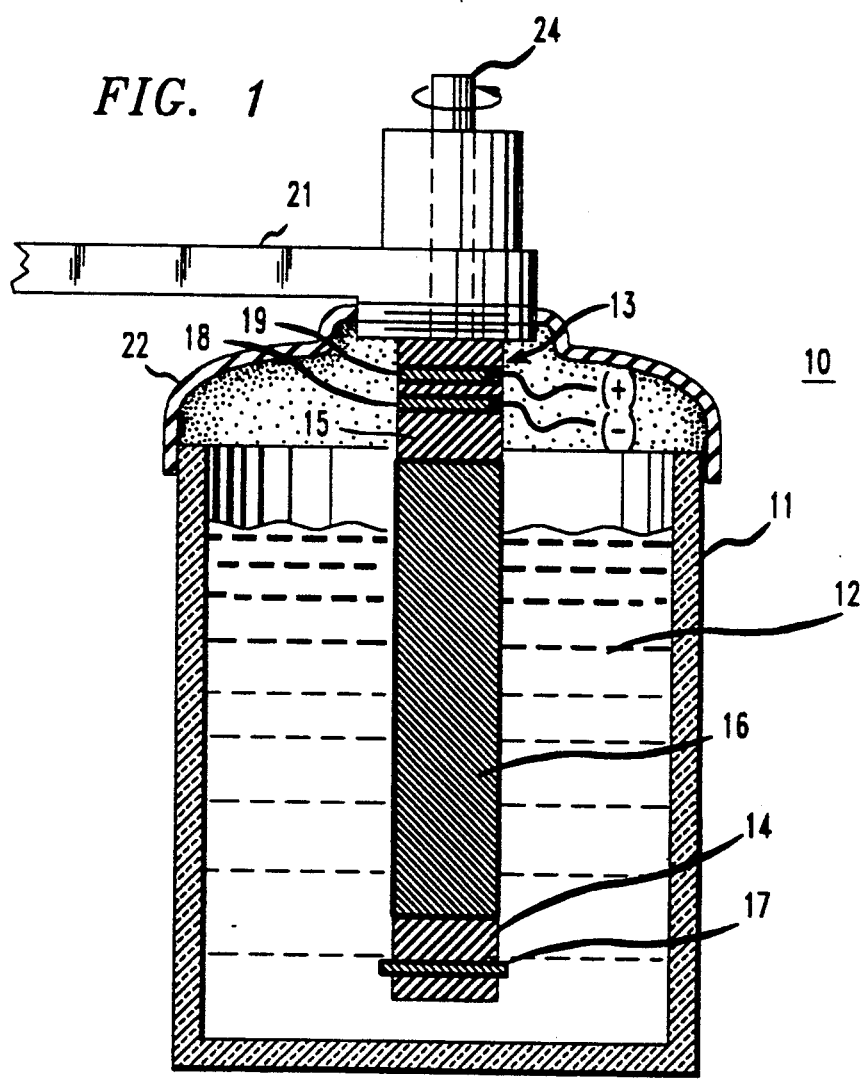
FIG. 1 is a schematic representation of a HMH cell.

The HMH cell is schematically presented in FIG. 1. The cell, 10, includes a container, 11, for holding electrolyte, 12, and an elongated, cylindrically-shaped measuring instrument, 13, suspended vertically in the container. The instrument is capable of being rotated about its longitudinal central axis.

Instrument 13 includes an elongated cylinder, 15, of a suitable insulating material, a sleeve-like metal cathode, 16, arranged coaxially on the cylinder, and a metal anode, 17, positioned at a lower end of cylinder 15 coaxially with it and in a longitudinally spaced relation to the cathode. Two sliding electrode contacts ("slip rings"), 18 and 19, on the cylinder are provided above cathode 16 as current collectors for the cathode and the anode, respectively. Upper part of cylinder 15 is securable to an arm, 21, of a support arrangement (not shown). Arm 21 supports instrument 13 suspended within container 11 and includes a cover 22 and a suitable drive means, such as a belt drive or a motor (not shown). Cover 22 encloses container 11 and assists in positioning instrument 13 coaxially of container 11. Drive means is for providing rotation to instrument 13 about its longitudinal central axis at a desired rate. The rate of rotation may be selected to be within a range from 10 to 10,000 RPM.

Cathode 16 includes a flexible test panel, 212, (FIG. 21) removably affixable to cylinder 15. This may be accomplished in various ways, two of which are as follows. In one instance opposite vertical ends of a flexible test panel may be inserted into a vertical longitudinal slot (not shown) in the surface of cylinder 15 while conforming the panel to the circumference of the cylinder. Alternatively, horizontal ends of the test panel conformed to the circumference of the cylinder may be secured by means of suitable fasteners (not shown). Such fasteners may include rubber bands which are slid over end portions of the panel. Electrical contact to the test panel may be provided by at least one conductive contact embedded into the surface of the cylinder, such as an area, a ring or a sleeve. The contact area, ring or sleeve is electrically connected to slip ring 18, such as via a conductor, 213 (FIG. 21), placed internally of the cylinder.

Anode 17 is positioned below cathode 16 and is spaced from it by means of a relatively short length of insulating cylinder 15. The spacing should not be less than that required to avoid undue bubbling at the space between the anode and the cathode. An excessive spacing is undesirable since it could adversely affect electric field distribution. A spacing of from 2 to 20 mm is useful, with 5-10 mm being preferred. Anode 17 is shown in FIG. 1 as being secured near the end of cylinder 15. Anode 17 may be secured to the cylinder in any suitable manner. This may involve a metallic fastener, such as a bolt exposed to the electrolyte or hidden within a removable insulating disc or an insulating disc provided with a threaded portion for mating with its counterpart in cylinder 15. The type of fastening anode 17 to the cylinder is not important so long as anode 17 is supplied with energy, for example, via slip ring 19. This may be accomplished by connecting anode 17 and slip ring 19 by a conductor (not shown) placed internally of cylinder 15. In FIG. 1, anode 17 is shown in the form of a thin disc, the radius of which is from 2 to 5 mm greater than the radius of cylinder 15. Other sizes and forms of anode 17 may be useful. For example, radial dimension of the disc may be equal or even smaller than that of cylinder 15. Also, the thickness of anode 17 may vary over a relatively large range. The important prerequisite is the symmetric geometry of anode 17 about the longitudinal axis of cylinder 15 in order to distribute the electric field uniformly about the anode.

Figure 21:
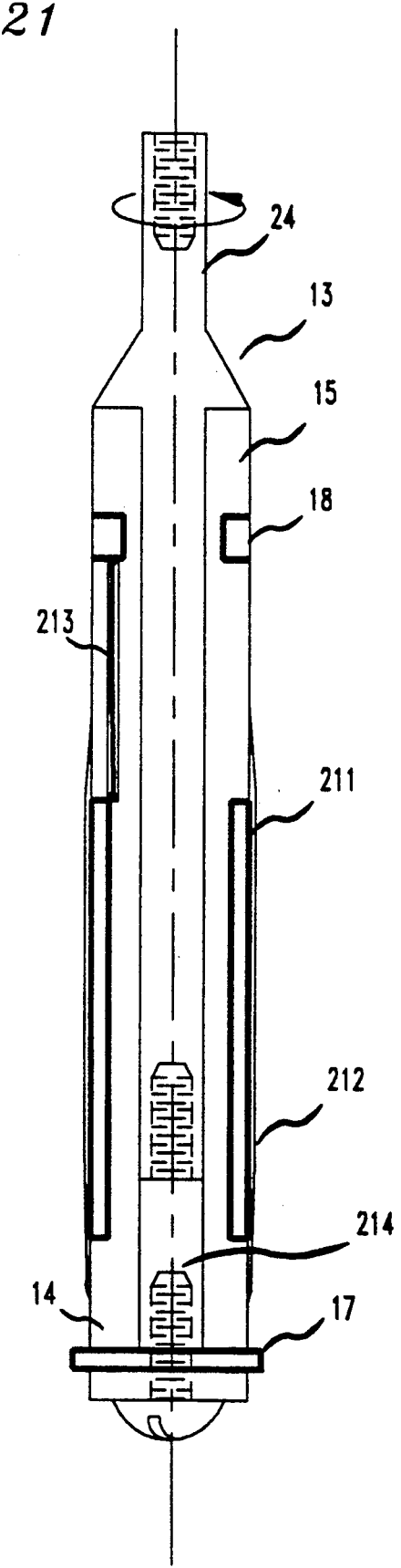
FIG. 21 is a schematic representation of a preferred embodiment of the measuring instrument being used in the HMH cell.

Cylinder 15 may be provided with an internal rod or shaft placed along the longitudinal axis of the cylinder (e.g., see FIG. 21). The rod or shaft may be needed to reinforce the cylinder and to provide means for imparting rotation to the cylinder. A metal rod or shaft may act as a conductor for connecting anode 17 to slip ring 19.

Cylinder 15 is made of an insulating material which is not adversely affected by the plating reaction, is non-conducting and non-contaminating with respect to the solution and the resultant metal deposit. Suitable material for the cylinder may be selected from such insulating materials as epoxy, polyethylene, polypropylene, polyvinyl chloride, teflon, fiberglass and other plastic materials possessing the above qualities. Container 11 and cover 22 are also of a material which is resistant to the effects of the electroplating solution and is non-conductive and non-contaminating with respect to the solution and the deposit. Suitable materials for the container and for the cover may be selected from such materials as glass, glazed ceramics, plastics, such as epoxy, polyethylene, polypropylene, polyvinyl chloride, teflon, fiberglass and other materials possessing the above qualities. The size of the container is at least such that the test panel is only partially immersed in a predetermined volume of an electroplating solution, e.g. about up to 80-90 percent of the panel height may be submerged in the solution. The panel is partially submerged so that a metal interface can be exposed to the solution and to the atmosphere above it for the purpose of a qualitative testing of the process. Typically, judgements are made about the corrosive action of the solution on the basis of the effects of the vapors evolved from the bath. Also some contaminants can be identified only by their effect on the panel at the liquid/air interface only.

Dimensions of test panel 212 (FIG. 21) being used in the HMH cell typically approximate dimensions of test panels in a Hull cell. For example, in a 267 ml. Hull cell, the cathode size is 3" high by 4 1/16" long (of which only up to $2\frac{1}{4}$" is immersed). In a HMH cell with 20 mm diameter cylinder, the panel may be $4\frac{1}{2}$" high and $2\frac{1}{2}$-$2\frac{3}{4}$" wide, of which only 4" may be immersed. Other sizes may be used as well.

Figure 31:
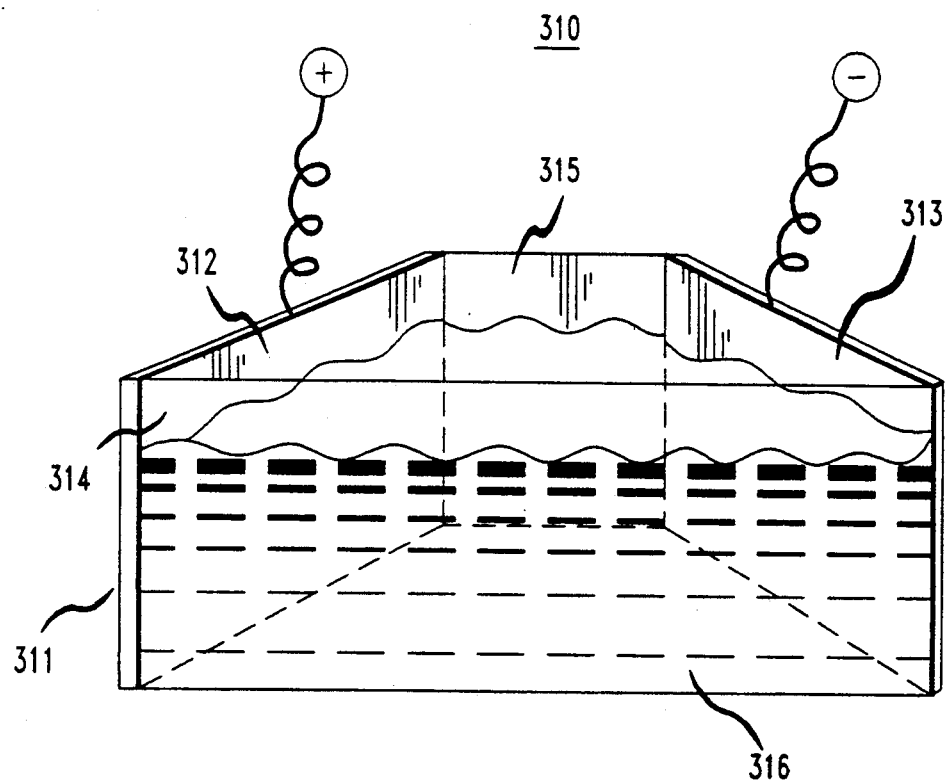
FIG. 31 is a schematic representation of the standard Hull cell.
Figure 32:
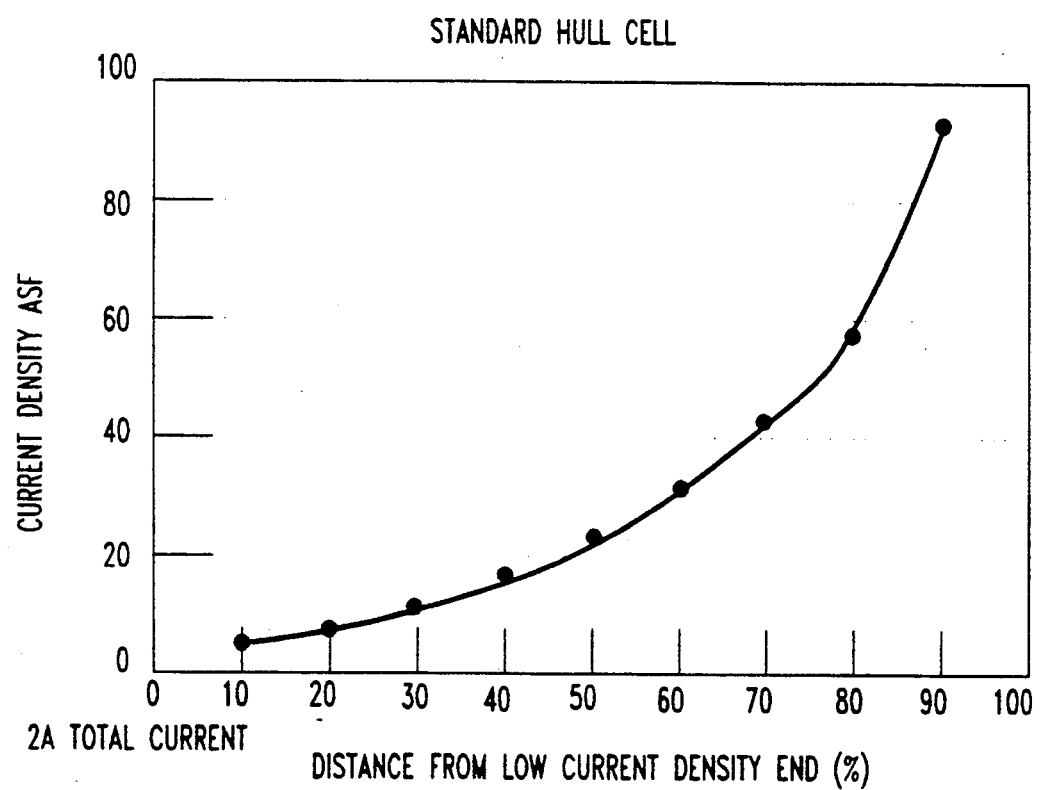
FIG. 32 is a schematic representation of a current density distribution along a test panel in a standard Hull cell.
Figure 33:
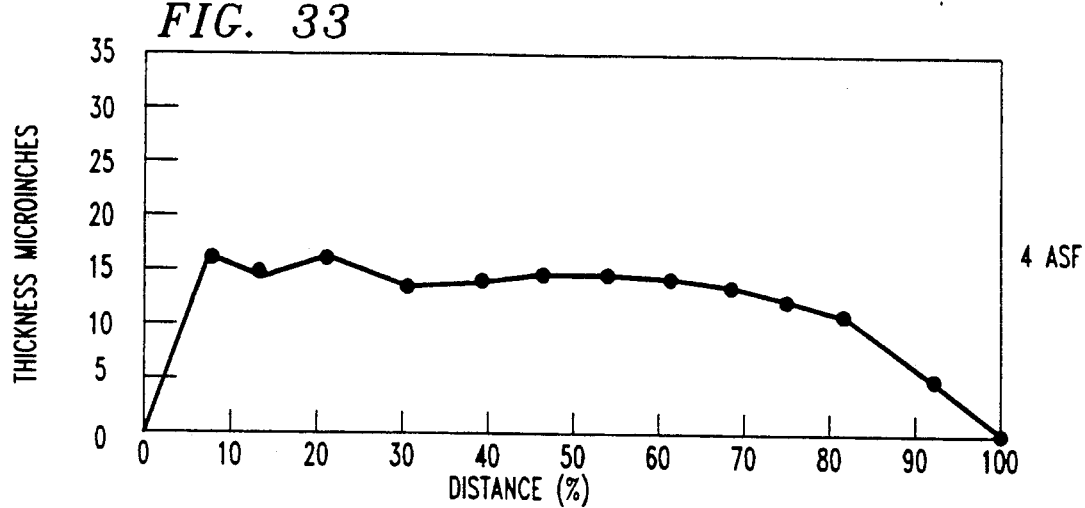
FIGS. 33, 34 and 35 are a sequence of three charts presenting deposit thickness distribution on a test panel deposited in a standard Hull cell at positions corresponding to 4, 20 and 80 ASF, respectively, and a total applied current of 2A.
Figure 34:
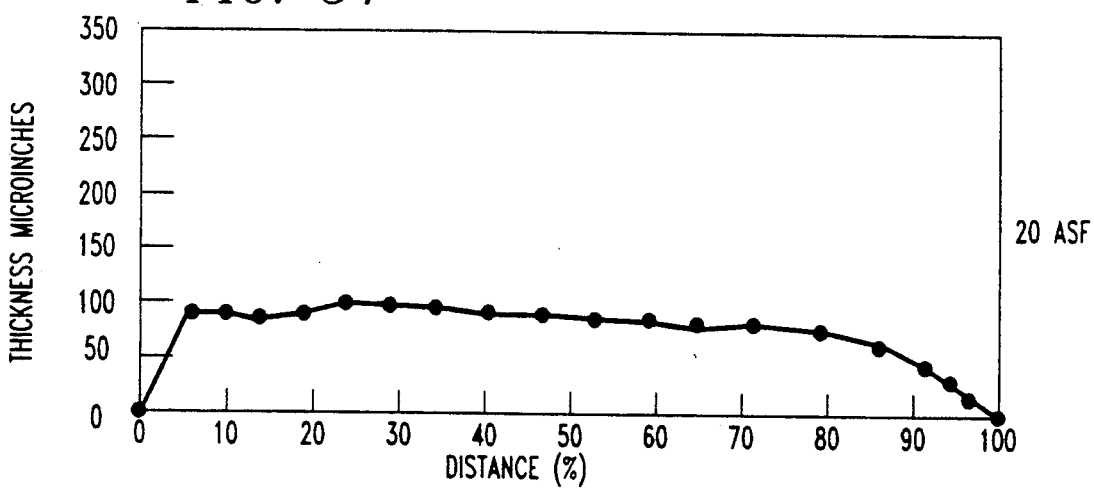
Figure 35:
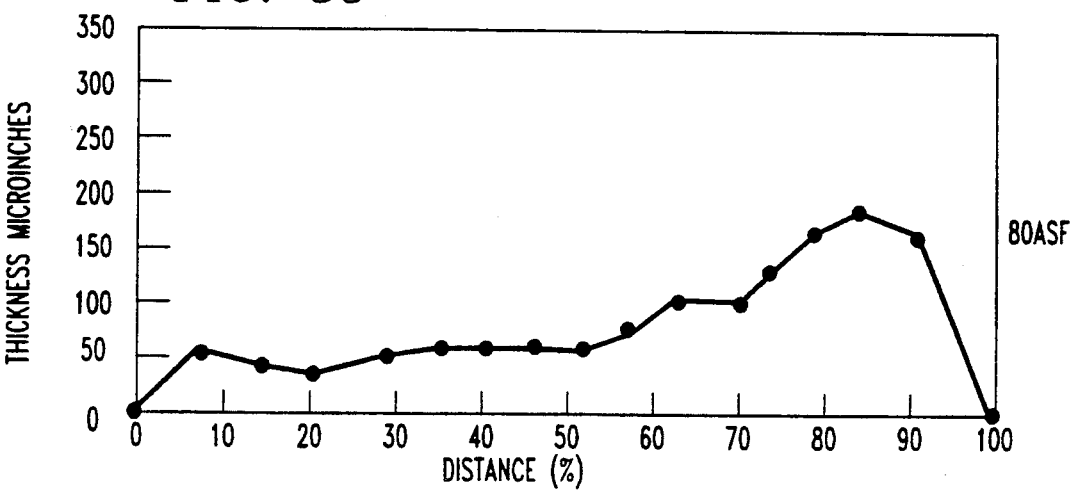

In order to compare the primary current distribution resulting from the design of the HMH cell with that of the standard Hull cell of FIG. 31, a number of variants of the HMH cell shown in FIG. 1 were analized using a software program commercially available from L-Chem Inc., 13909 Larchmere Blvd., Shaker Heights, OH 44120, U.S.A. Also see, W. Michael Lynes and Uziel Landau, "A Novel Adaptation of the Finite Difference Method for Accurate Description of Non-Orthogonal Boundaries", The Electrochemical Society, Fall Meeting, Chicago, 1988, Abstract 332. The results of the analyses are presented for each specific variant in two graphs, one representing electric field distribution and the other the current density distribution. The resulting current density distribution for each variant was compared with one (FIG. 32) for the standard Hull cell.

The low current density end in the HMH cell is that end of the test panel which is the farthest from the anode.

Figure 2:
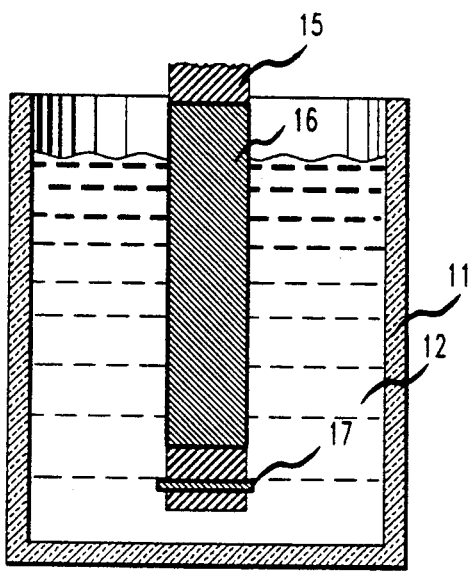
FIG. 2 is a schematic representation of a HMH cell with a partially submerged test panel.
Figure 3:
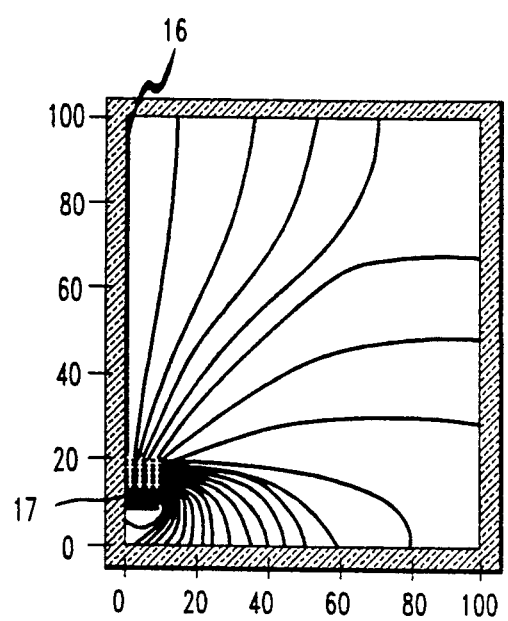
FIG. 3 is a schematic representation of an electric field distribution in the HMH cell of FIG. 2.
Figure 4:
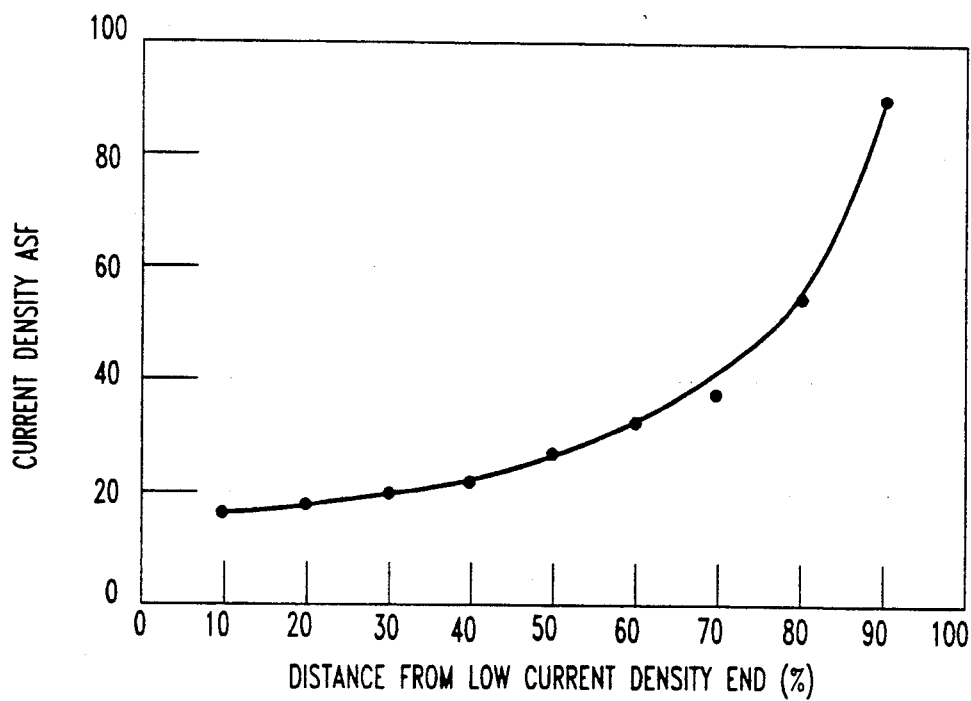
FIG. 4 is a schematic representation of a current density distribution along a test panel in HMH cell of FIG. 2.

Comparison of the current density distribution presented in FIG. 4 for the variant with partially submerged panel, shown in FIG. 2, to the current density distribution (FIG. 32) in the standard Hull cell showed that the current density distribution of this embodiment effectively approximated the current density distribution results of the Hull cell. This embodiment was considered viable for use in place of the Hull cell; however, even closer approximation was desired.

Figure 5:
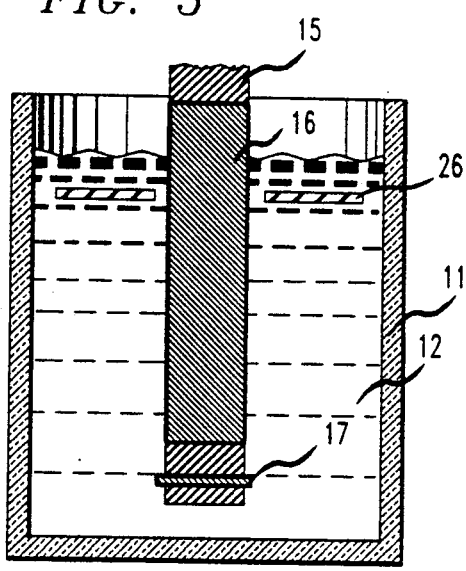
FIG. 5 is a schematic representation of a HMH cell with a partially submerged test panel and one horizontal baffle.
Figure 6:
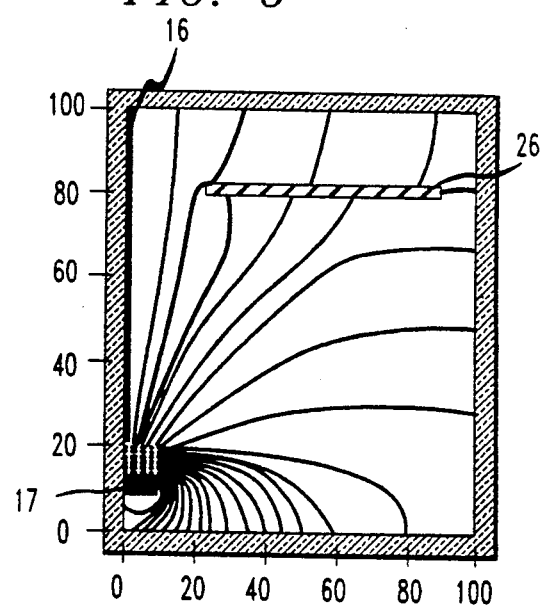
FIG. 6 is a schematic representation of an electric field distribution in the HMH cell of FIG. 5.
Figure 7:
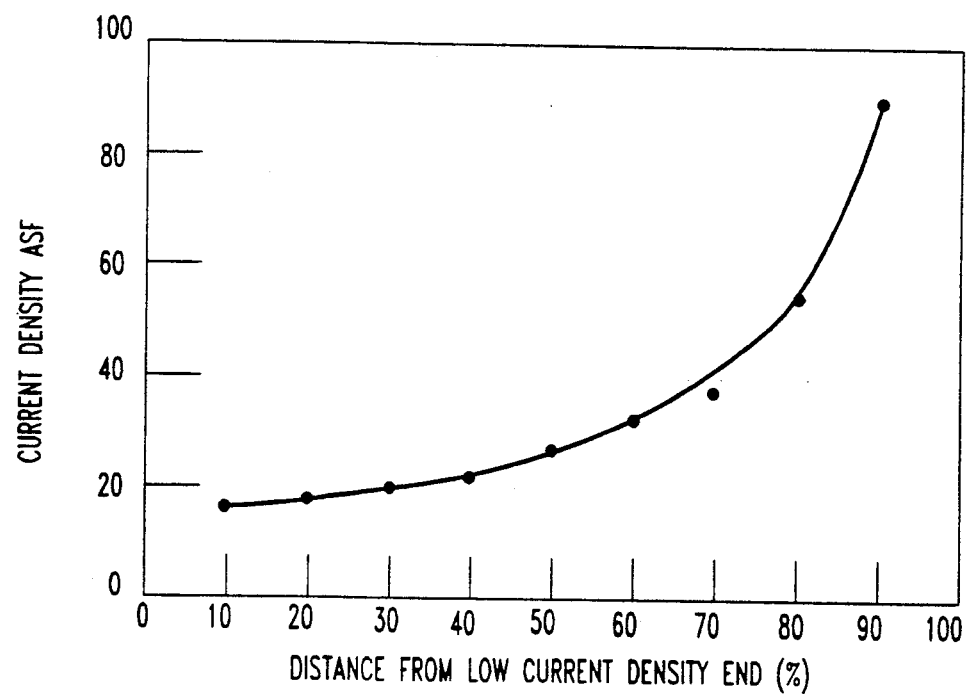
FIG. 7 is a schematic representation of a current density distribution along a test panel in HMH cell of FIG. 5.
Figure 8:
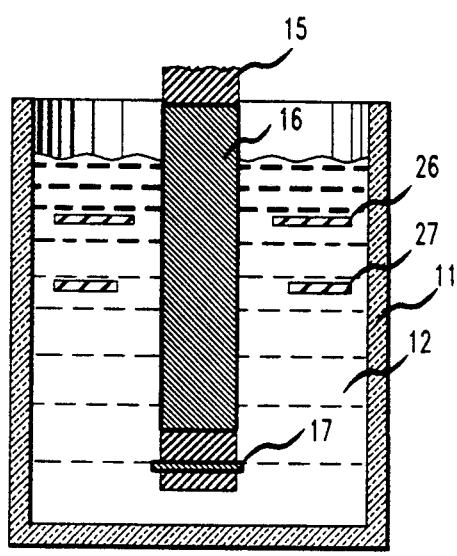
FIG. 8 is a schematic representation of a HMH cell with a partially submerged test panel and two horizontal baffles.
Figure 9:
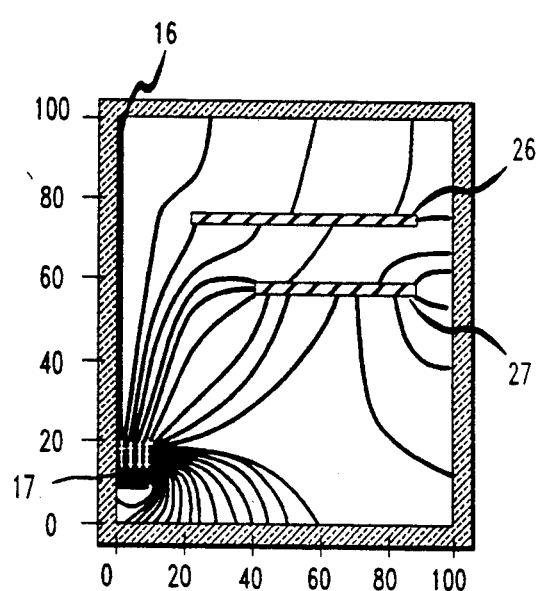
FIG. 9 is a schematic representation of an electric field distribution in the HMH cell of FIG. 8.
Figure 10:
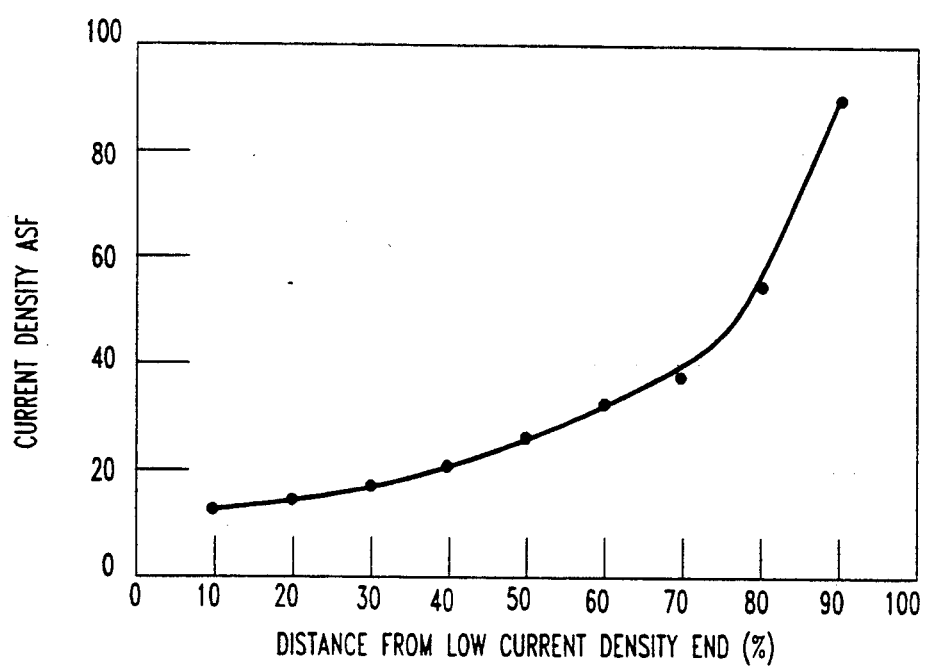
FIG. 10 is a schematic representation of a current density distribution along a test panel in HMH cell of FIG. 8.
Figure 11:
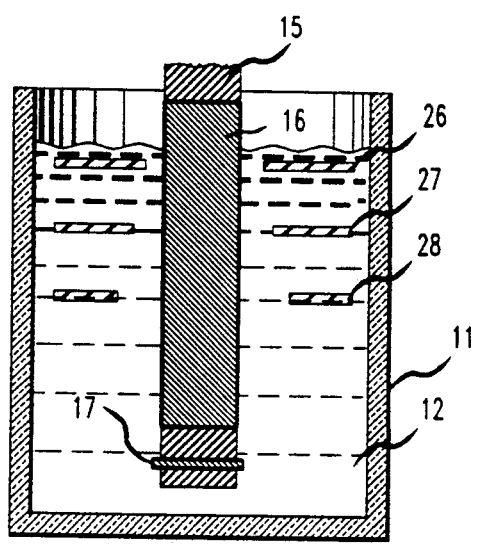
FIG. 11 is a schematic representation of a HMH cell with a partially submerged test panel and three horizontal baffles.
Figure 12:
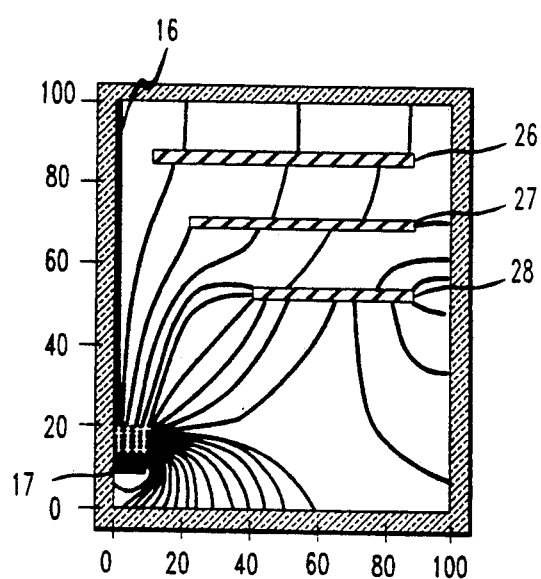
FIG. 12 is a schematic representation of an electric field distribution in the HMH cell of FIG. 11.
Figure 13:
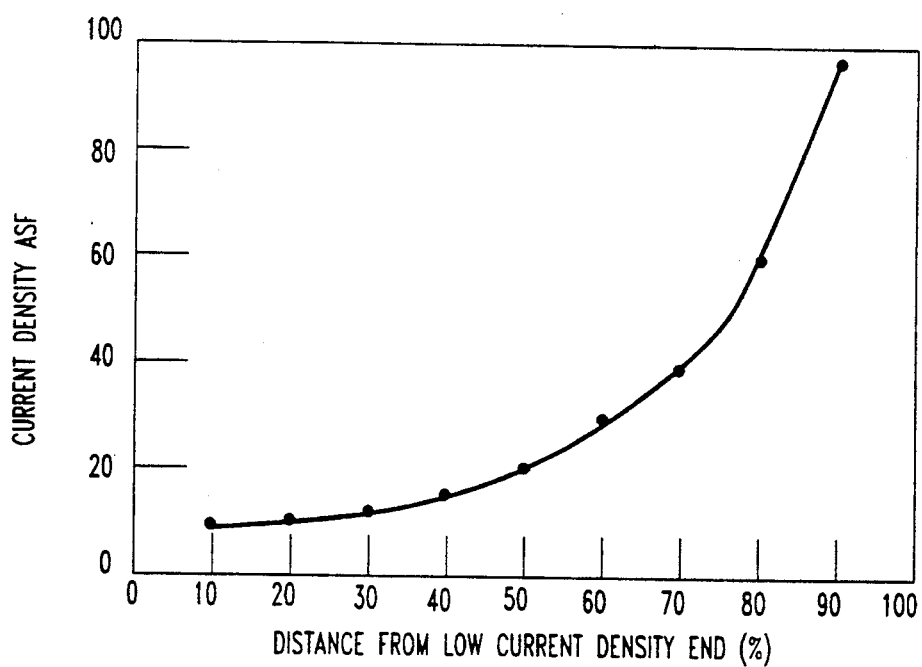
FIG. 13 is a schematic representation of a current density distribution along a test panel in HMH cell of FIG. 11.

Much closer approximation was obtained by the use of a partially submerged test panel with one or more horizontal baffles. These baffles represent minimal restriction to the flow of liquid while acting as a good shield to the electric field. The combination with one horizontal baffle (FIG. 5) shows that the actual current density distribution (FIG. 7) is very close to the one (FIG. 32) obtainable with the standard Hull cell. FIG. 10 shows that with two horizontal baffles, 26 and 27, the actual current density distribution (FIG. 8) is even closer to the one (FIG. 32) obtainable with the standard Hull Cell. FIG. 13 shows that with three horizontal baffles, 26, 27 and 28, (FIG. 11) an excellent agreement with the Hull cell current density distribution (FIG. 32) was achieved. This combination was selected for our testing and further optimization.

Figure 14:
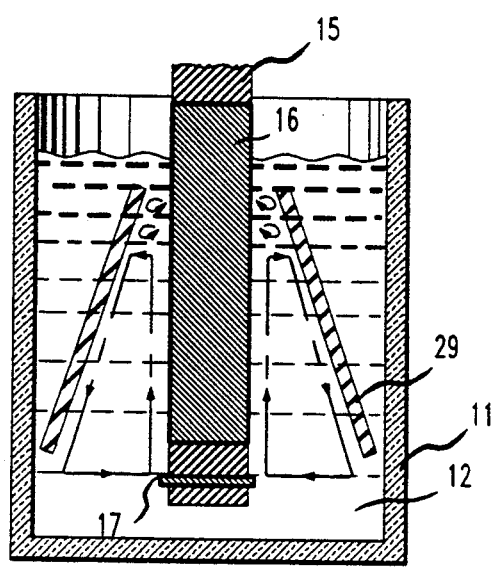
FIG. 14 is a schematic representation of a HMH cell with an insulating cone shield.
Figure 15:
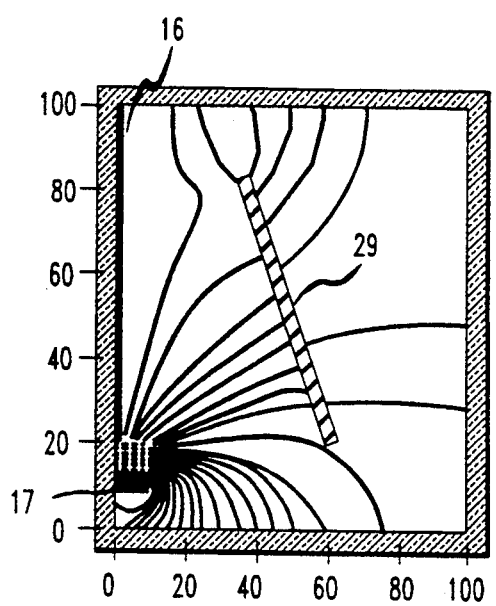
FIG. 15 is a schematic representation of an electric field distribution in the HMH cell of FIG. 14.
Figure 16:
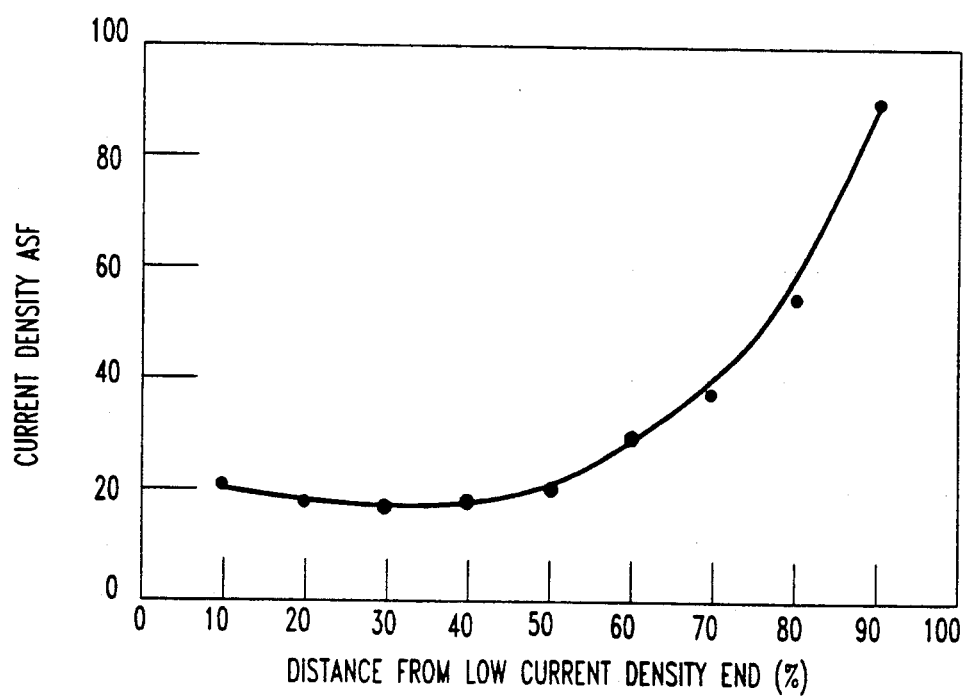
FIG. 16 is a schematic representation of a current density distribution along a test panel in HMH cell of FIG. 14.

A variant with an insulating cone-shield, 29, placed about instrument 13 as presented in FIG. 14 seemed to be a natural extension of the Hull cell design, namely, because the wall of the insulating cone is at an acute angle to the low density end of the cathode. However, with a cone-shield one obtains non-uniform hydrodynamics along the test panel. The cone-shield about the cylinder leads to a continuously varying geometry, thus, if a cone-shield is applied about the rotating cylinder, one can simultaneously obtain a whole range of hydrodynamic conditions over the test panel. The probable type of liquid flow is schematically presented in FIG. 14. Since the need for the uniform and controlled hydrodynamics in the HMH cell is the dominant factor, the cone shield with non-uniform hydrodynamics is not a suitable arrangement. In addition, the use of the cone shield demonstrated (FIG. 16) an inferior performance for developing the current density distribution pattern for Hull cell simulation.

Figure 17:
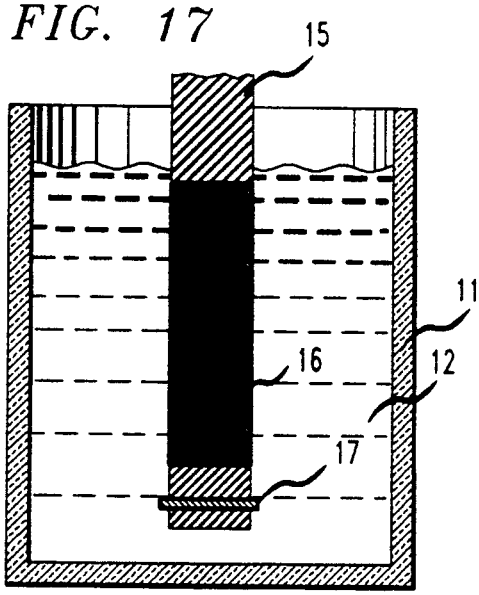
FIG. 17 is a schematic representation of a HMH cell with a completely submerged test panel.
Figure 18:
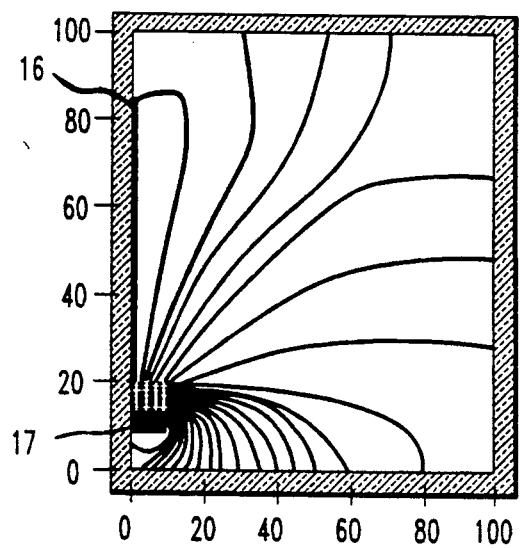
FIG. 18 is a schematic representation of an electric field distribution in the HMH cell of FIG. 17.
Figure 19:
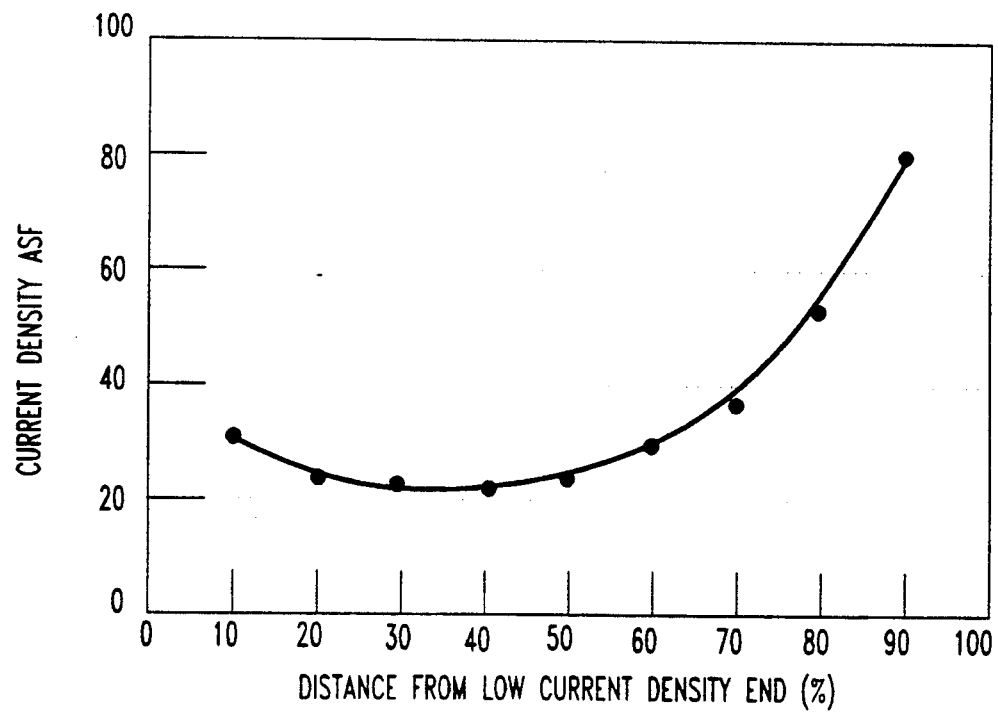
FIG. 19 is a schematic representation of a current density distribution along a test panel in HMH cell of FIG. 17.

An attempt to utilize the HMH cell with a test panel completely submerged in the electrolyte (FIG. 17) showed that the current distribution (FIG. 19) for submerged panel is clearly inferior to the one (FIG. 4) obtained with the partially submerged panel. The reason resides mostly in the "edge effect" which takes the primary current to infinity for a submerged electrode edge with a parallel or no insulator at all. In a partially submerged panel this edge effect is reduced by the solution surface which acts as an insulator perpendicular to the panel giving current density a finite value.

Figure 20:
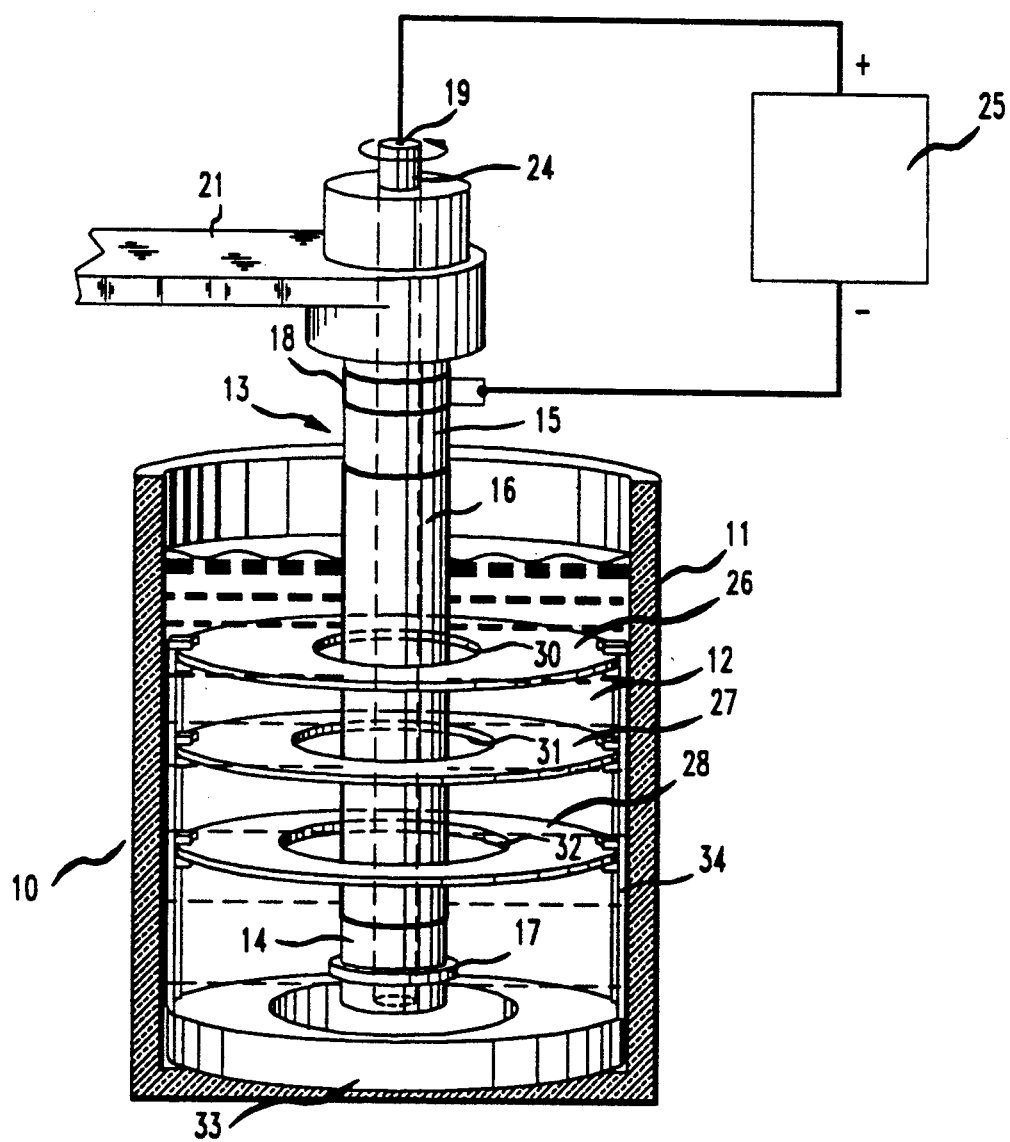
FIG. 20 is a schematic perspective representation of a preferred embodiment of the HMH cell with three horizontal baffles.

The embodiment with partially immersed panel and three horizontal baffles was rated the highest of these variants relative to the standard Hull cell and was chosen for further testing. This embodiment is shown in FIGS. 20 and 21. In these FIGs. the same numerals denote the same elements as those disclosed in FIGS. 1, 5, 8 and 11.

Cell 10 includes insulating container 11 holding electrolyte 12 in which is suspended measuring instrument 13. The measuring element comprises elongated insulating cylinder 15, a drive shaft, 24, arranged within and coaxially with the longitudinal central axis of the cylinder, and anode electrode 17 secured to shaft 24 at the bottom of the cylinder coaxially thereof. In this embodiment, anode 17 is in the form of a thin disk which extends a distance of from 2 to 5 mm beyond the circumference of the cylinder, diameter of which may vary over a wide range, including from 10 to 50 mm, preferably 20 mm, depending on the size of the cell and the volume of electrolyte therein. Other forms of anode 17 are useful as well, such as a disc or a ring having the same or smaller radial dimension as the cylinder. The important criteria is that both the anode and the cathode are arranged coaxially on the longitudinal axis of the cylinder in spaced relation each to another. Cathode 16 includes a sleeve, 211, of refractory metal embedded into cylinder 15 and is used for providing electrical contact to detachable test panel 212. The test panel is of a metal which does not react with the solution, such as copper or stainless steel. The sleeve is of refractory metal selected from such metals as titanium, tantalum, nobium, aluminum which form a thin layer of oxide on their surface and thus, restrict plating of deposits on their surface. Other materials such as graphite or glassy carbon, stainless steel, or thin coating of the refractory metals on another metal substrate, are also useful. A slip ring, 18, mounted on the cylinder above the sleeve is electrically connected to and is used as a current carrier for the sleeve. Slip ring 18 is connectable to a negative (cathode) terminal of an energy source, 25, e.g. a rectifier.

Drive shaft 24 is preferably of a metal and provides the positive voltage to anode 17. Drive shaft 24 is connected to the positive (anode) side of energy source 25. Typically, the drive shaft is of a metal selected from stainless steel or brass. To avoid electrolyte attack on a lower portion, 214, of the drive shaft adjacent to the anode, the lower portion of the drive shaft may be made of the same metal as sleeve 211. Alternatively, the drive shaft may be of a rigid insulating material which is non-contaminating to the solution, with electrical connection provided to anode 17 via a conductor (not shown) inside of the shaft or of the cylinder. The connection may be to slip ring 19 (FIG. 1) on the cylinder 15 or on that portion of the insulating shaft which projects from the cylinder or via some other suitable means. Suitable material for the non-conducting shaft may be selected from such insulating materials as epoxy, polyethylene, polypropylene, polyvinyl chloride, teflon, fiberglass and other plastic materials.

In the preferred embodiment with partially immersed test panel (cathode) and three baffles, shown schematically in FIG. 20, cell 10 includes a baffle assembly including baffles 26, 27 and 28 arranged within container 11 horizontally about cylinder 13 at vertically spaced intervals each from another. For example, first baffle 26 is about 5 to 15 mm from the surface of electrolyte 14, second baffle 27 is 10 to 20 mm from the first baffle, and the third, lower baffle 28 is 10 to 30 mm from the second baffle. The baffles are made in the form of annular discs each having a central opening, 30, 31 and 32, respectively, so that each successive baffle is spaced from the wall of cylinder 11, a distance greater than each preceding baffle. Central opening, 30, 31 or 32, of each succeeding baffle is progressively larger so that the body of each successive baffle is spaced progressively greater distance from the cylinder. For example, first baffle 26 is spaced 5 to 15, preferably 10 mm from cylinder 13, second baffle 27 is spaced 10 to 20, preferably 15 mm from the cylinder and third baffle is spaced 15 to 25, preferably 20 mm from the cylinder. A circular bottom anker 33 and at least two spacer connectors 34 complete the baffle assembly. Alternatively, the baffles may be suspended from the rim of the container. Still alternatively the baffle assembly may be in a form of a single spiral baffle beginning at one upper corner corresponding to the position of baffle 26 and spirally proceeding downwardly about the instrument 13 while an inwardly facing edge of the spiral baffle follows a progressively increasing spacing distance from instrument 13. The baffles are made of insulating material which is unaffected by the plating reaction and which does not contaminate the plating solution. Suitable material may be selected from such insulating materials as glass, glazed ceramic, plastics, such as polyethylene, polypropylene, polyvinylchloride, teflon, fiberglass and other plastic materials.

In a HMH cell holding 500 ml of plating solution, baffles 26, 27 and 28 are positioned, in a descending order, at 10, 20 and 30 mm from the top of the solution level in the container and are spaced radially 5, 10 and 15 mm from cylinder 11, respectively. Outer edge of each baffle is spaced from the walls of container 11 on the order from 1 to 10 mm sufficiently to permit at least some movement of the liquid between each baffle and the wall of container 11. For cells with a different volume, these dimensions could vary.

Figure 22:
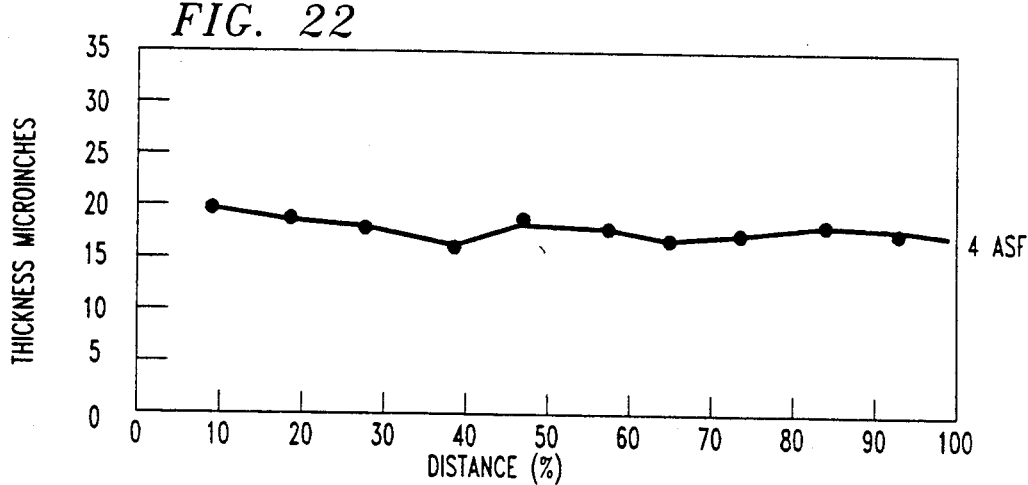
FIGS. 22, 23 and 24 are a sequence of three charts presenting deposit thickness distribution on a test panel deposited in a HMH cell with three horizontal baffles at positions corresponding to 4, 20 and 80 ASF, respectively, and a total applied current of 2A.
Figure 23:
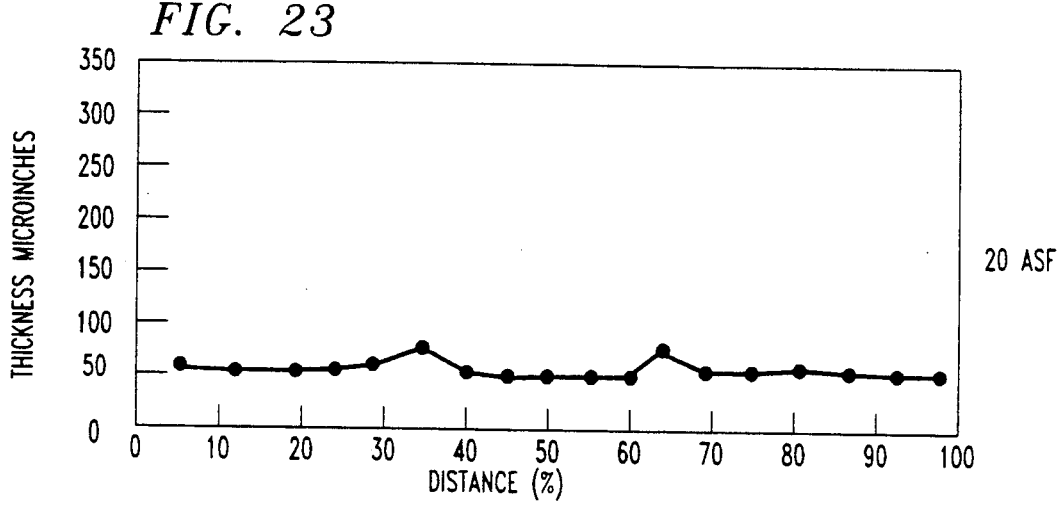
Figure 24:
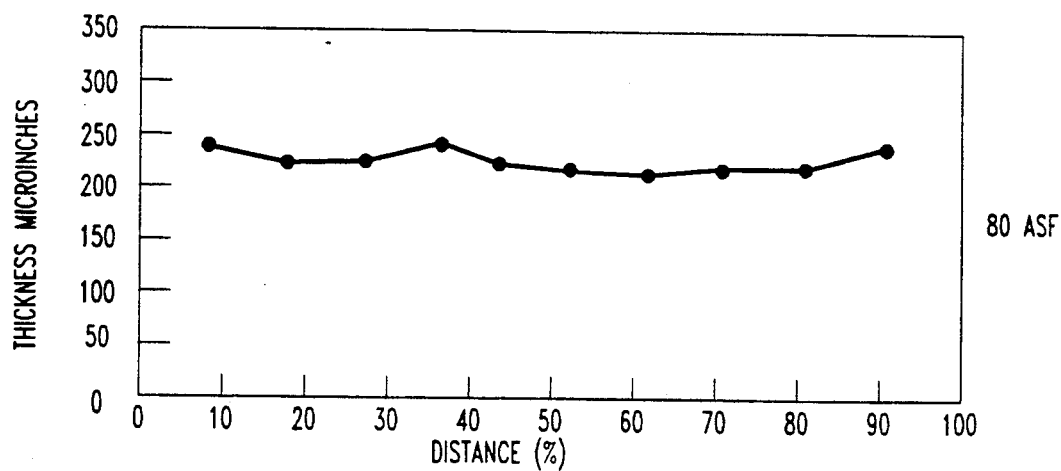

In FIGS. 22, 23 and 24 are shown measurements of the thickness distribution across panel 22 at three separate current density level positions corresponding to 4, 20 and 80 ASF, respectively, at a total applied current of 2A. In contrast to thickness distribution measurements on the Hull cell panel for the same current density level positions (FIG. 32), these measurements indicate a very uniform distribution of thickness across these specific current density levels on the panel. The measurements of the current density distribution based on measurements of thickness distribution across a palladium panel plated from a proprietary plating process closely correspond to the calculated values of current density distribution shown in FIG. 13. The similarity to the actual Hull cell current density distribution (FIG. 32) is quite evident.

Figure 25:
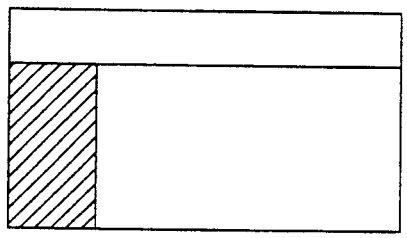
FIGS. 25, 26 and 27 are a comparison of burned deposit on a high current density portion of a test panel in a standard Hull cell (FIG. 25) with that on a test panel in a HMH cell at 10 and 100 cm/s liquid velocity (FIGS. 26 and 27, respectively) from an aqueous solution containing 25 g/l Pd at 40° and with a pH 7.5.
Figure 26:
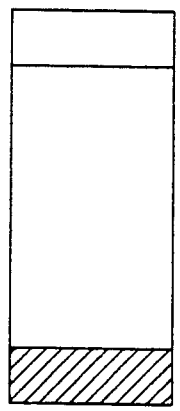
Figure 27:
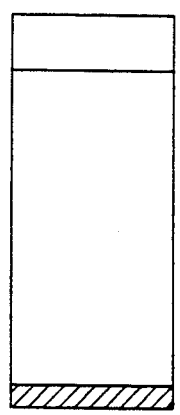

In FIGS. 25, 26 and 27 are shown deposition patterns obtained with the standard Hull cell (FIG. 25) and the HMH cell (FIGS. 26 and 27) from a high speed palladium plating bath containing 25 grams per liter Pd, pH of 7.5, with plating conducted at 40° C. The panel plated at 10 cm/sec liquid velocity (FIG. 26) shows almost identical pattern as the one obtained with the standard Hull cell. The 100 cm/sec panel (FIG. 27) shows a decreased level of burning and dullness at the high current density end. This is to be expected if such features as burning and dullness on the panel are a result of the mass transport at the interface. Lack of dullness across the panel also means that the particular bath had no other contaminants which could be detrimental at increased velocity.

Figure 28:
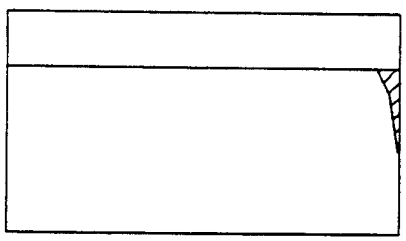
FIGS. 28, 29 and 30 are a schematic comparison of impurities effect on a low current density portion of a test panel in a standard Hull cell (FIG. 28) with that of a test panel in a HMH cell at 10 and 100 cm/s liquid velocity (FIGS. 29 and 30, respectively) from an aqueous solution containing nickel sulfamate at 45° C., with pH=4.0 and with 100 ppm of copper as an impurity.
Figure 29:
Figure 30:
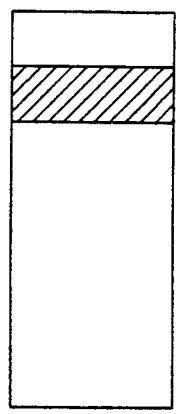

In FIGS. 28, 29 and 30 are shown deposition patterns obtained with the standard Hull cell (FIG. 28) and the HMH cell (FIGS. 29 and 30) from a nickel electroplating bath that had copper contamination. Nickel was deposited at 45° C. from a plating bath containing nickel sulfamate, pH of 4.0 and 100 ppm of copper contamination. Approximately 100 ppm Cu is barely noticeable on the panel in standard Hull cell (FIG. 28) and on the 10 cm/sec HMH cell panel (FIG. 29). At 100 cm/sec ¾" (1.9 cm) of low current density side of the HMH cell panel plate had dull coppery finish (FIG. 30). Hence, the contamination was clearly evident and the range of current densities that could be applied for its removal would be easily determined.

These results indicate that HMH can give a current distribution analogous to the one obtained with standard Hull cell but with an improved control over the transport of matter across the interface. In addition HMH, as a tool, opens up new avenues for future exploration and quality control of electroplating solutions.

We claim:

1. An electroplating test cell for determining quality of electroplated deposits simultaneously in a wide range of current densities at a desired total applied current value, comprising
    (a) a container of non-conducting, non-contaminating material for holding an electrolyte,
    (b) an elongated cylindrically-shaped measuring instrument adapted to be rotated about its longitudinal central axis, the instrument comprising in descending order along said central axis coaxially arranged
        an elongated upper electrically non-conducting section,
        an elongated electrically conducting cathode section extending coaxially along a major portion of the measuring instrument,
        a short lower electrically non-conducting spacer section, and
        a short electrically conducting anode section, said spacer section electrically separating the anode section from the cathode section and having essentially the same diameter as the cathode section, and
        contact means connectable to a source of energy for providing current separately to the cathode and to the anode section, at least one of said contact means being on the non-conducting upper section in spaced relationship to the cathode section,
        the length of said cathode section is such that, when immersed in a predetermined volume of the electrolyte in the container, from 10 to 20 percent of the cathode section is exposed above the level of the electrolyte in the container, and
    (c) at least one baffle arranged about and coaxially with said elongated cylindrical instrument, an inner edge of said at least one baffle being spaced from the elongated cylindrical instrument, and an outer edge of said at least one baffle being spaced from the wall of the container.

2. The cell of claim 1, in which said at least one baffle comprises at least one annular baffle disc placed horizontally about and coaxially of the cathode.

3. The cell of claim 2, in which at least two baffle discs are vertically spaced each from another, each successive baffle disc having a central opening which is greater than that of the preceding disc.

4. The cell of claim 3, in which three baffle discs are placed about the cylinder.

5. The cell of claim 1, in which said at least one baffle is in the form of a flat band spirally arranged about the instrument with the inner edge of the baffle being progressively further positioned from the instrument.

6. An electroplating test cell for determining quality of electroplated deposits simultaneously in a wide range of current densities at a desired total applied current value, comprising a container of non-conducting non-contaminating material for holding an electrolyte, and a measuring instrument comprising:

an elongated cylinder of an electrically non-conducting material suspendable within the container, the central axis of the cylinder being substantially parallel to the central axis of the container, said cylinder being adapted to be rotated about its longitudinal central axis, a short metallic anode electrode secured to a lower portion of the cylinder coaxially of the cylinder, an elongated metallic cathode sleeve secured to the periphery and extending along a major portion of the cylinder coaxially thereof, a lower edge of the cathode sleeve being spaced along the said central axis from an upper edge of the anode electrode by a short electrically non-conducting spacer section, said spacer section having essentially the same diameter as said cathode sleeve, the length of said cathode sleeve is such that, when immersed in the electrolyte, from 10 to 20 percent of the cathode sleeve is exposed above the level of the electrolyte, means for providing current to the anode electrode and the cathode sleeve, respectively, and at least one baffle is arranged about and coaxially with the said elongated cylinder, an inner edge of said at least one baffle being spaced from the cylinder.

7. The cell of claim 6, in which said at least one baffle comprises at lease one annular baffle disc placed horizontally about and coaxially of the cathode.

8. The cell of claim 7, in which at least two baffle discs are vertically spaced each from another, each successive baffle disc having a central opening which is greater than that of each preceding baffle.

9. The cell of claim 8, in which three baffle discs are placed about the cylinder.

10. The cell of claim 6, in which said at least one baffle is in the form of a flat band spirally arranged about the instrument with the inner edge of the baffle being progressively further positioned from the instrument.

* * * * *